United States Patent
Leuthardt et al.

(10) Patent No.: US 9,227,043 B2
(45) Date of Patent: Jan. 5, 2016

(54) CATHETER ASSEMBLY FOR USE WITH SHUNT SYSTEMS AND METHOD OF USING SAME

(71) Applicant: Washington University, St. Louis, MO (US)

(72) Inventors: Eric Leuthardt, St. Louis, MO (US); Guy Genin, St. Louis, MO (US); Matthew Smyth, St. Louis, MO (US); David Limbrick, St. Louis, MO (US); Daniel Moran, St. Louis, MO (US); Lihong Wang, Creve Coeur, MO (US); Aaron McLaughlin, St. Louis, MO (US); Alexander Yang, St. Louis, MO (US); Manish Shah, St. Louis, MO (US); Devon Haydon, St. Louis, MO (US); Sam Stone, St. Louis, MO (US); Michael Winek, St. Louis, MO (US); Richard L. Marcus, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 311 days.

(21) Appl. No.: 13/678,769

(22) Filed: Nov. 16, 2012

(65) Prior Publication Data

US 2013/0131576 A1    May 23, 2013

Related U.S. Application Data

(60) Provisional application No. 61/561,377, filed on Nov. 18, 2011.

(51) Int. Cl.
*A61M 27/00*    (2006.01)
*A61M 1/00*    (2006.01)

(52) U.S. Cl.
CPC .................................. *A61M 27/006* (2013.01)

(58) Field of Classification Search
CPC ...... A61M 27/006; A61M 27/00; A61M 1/00
See application file for complete search history.

(56) References Cited

U.S. PATENT DOCUMENTS

| | | |
|---|---|---|
| 3,595,240 A | 7/1971 | Mishler |
| 5,207,684 A | 5/1993 | Nobles |
| 5,368,556 A | 11/1994 | Lecuyer |
| 5,607,407 A * | 3/1997 | Tolkoff et al. ................. 604/523 |
| 7,513,883 B2 | 4/2009 | Glenn |
| 7,524,298 B2 | 4/2009 | Gharib et al. |
| 7,582,068 B2 | 9/2009 | Koullick et al. |
| 7,766,855 B2 | 8/2010 | Miethke |
| 7,922,685 B2 | 4/2011 | Rosenberg |
| 7,976,517 B2 | 7/2011 | Dextradeur et al. |
| 8,002,730 B2 | 8/2011 | Moskowitz et al. |

(Continued)

*Primary Examiner* — Tatyana Zalukaeva
*Assistant Examiner* — Sara Sass
(74) *Attorney, Agent, or Firm* — Armstrong Teasdale LLP

(57) ABSTRACT

A catheter assembly for inserting in a fluid filled space in a body includes a main body having a first end portion and a second end portion. The first end portion is positionable within the fluid filled space and the second end portion is adapted to extend outward from the fluid filled space when the first end portion is positioned within the fluid filled space. The catheter assembly also includes a catheter tip that is connected to the second end portion. The catheter tip includes a housing having a cavity defined therein. The catheter tip also includes a rotating element positioned within the cavity. The rotating element is configured to rotate within the cavity to facilitate movement of the first end portion of the main body within the fluid filled space.

15 Claims, 4 Drawing Sheets

(56) References Cited

U.S. PATENT DOCUMENTS

| | | | |
|---|---|---|---|
| 2005/0240146 A1* | 10/2005 | Nash | A61B 17/32037 604/35 |
| 2008/0097276 A1 | 4/2008 | Bertrand et al. | |
| 2008/0132823 A1 | 6/2008 | Rosenberg | |
| 2008/0281250 A1 | 11/2008 | Bergsneider et al. | |
| 2009/0292276 A1* | 11/2009 | Nash | A61B 17/32037 606/7 |
| 2010/0222732 A1 | 9/2010 | Sevrain | |
| 2010/0228179 A1 | 9/2010 | Thomas et al. | |

\* cited by examiner

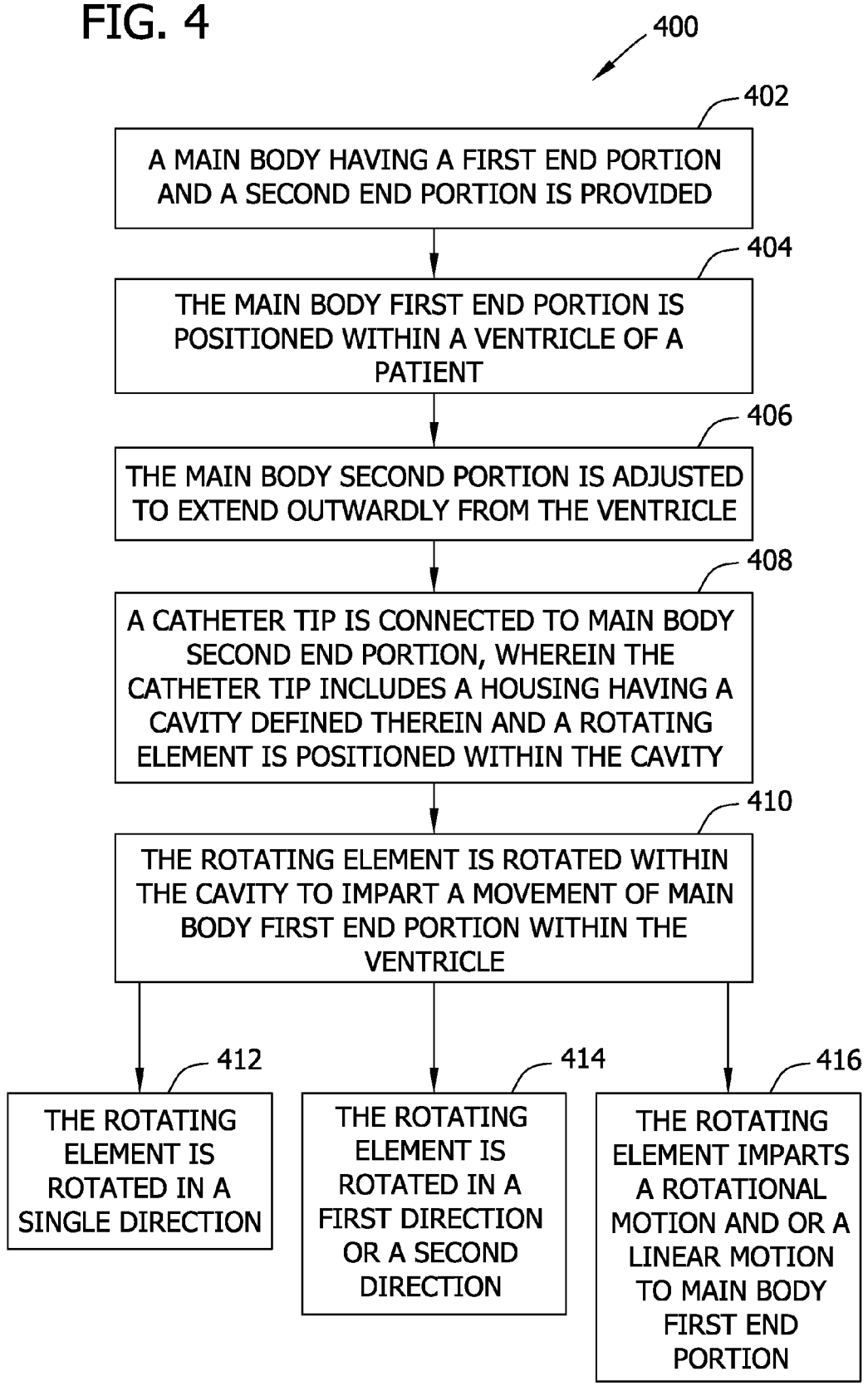

CATHETER ASSEMBLY FOR USE WITH SHUNT SYSTEMS AND METHOD OF USING SAME

CROSS REFERENCE TO RELATED APPLICATION

This application claims priority to U.S. provisional application No. 61/561,377 filed Nov. 18, 2011, which is incorporated herein in its entirety.

BACKGROUND OF THE INVENTION

The field of the invention relates generally to shunt systems and, more particularly, to a catheter assembly for use with shunt systems.

Approximately 75,000 people per year suffer from an accumulation of cerebrospinal fluid (CSF) within the ventricles in the brain. Such a condition is also known as hydrocephalus. Moreover, approximately 1 in 500 children are born with hydrocephalus. While there is no known cure for hydrocephalus, the condition is commonly treated with a shunt system, such as a ventriculoperitoneal shunt system, which facilitates the flow of CSF from the ventricles of the brain to the peritoneal cavity.

Such known shunt systems may include a catheter, e.g., a ventricular catheter, which is inserted into the brain, a valve to control the flow of CSF, and a peritoneal catheter that is inserted into the peritoneal cavity. In some cases, a catheter tip or reservoir, such as a Rickham reservoir, is attached to the ventricular catheter to stabilize the catheter and to serve as an access point for the CSF.

However, known shunt systems may wear and/or may become inoperable over time. For example, because the ventricular catheter is essentially immobile (i.e., fixed) within the ventricle, occlusion of the catheter may occur. The occlusion may be caused when tissues located within the brain, such as ependymal and choroid plexus tissues, adhere to the ventricular catheter. Such adherence may also occur within the catheter tubing. If occlusion occurs, the shunt system may be unable to adequately remove CSF from the brain.

BRIEF DESCRIPTION OF THE INVENTION

In one embodiment, a catheter assembly for inserting in a fluid filled space in a body generally comprises a main body having a first end portion and a second end portion. The first end portion is positionable within the fluid filled space and the second end portion is adapted to extend outward from the fluid filled space when the first end portion is positioned within the fluid filled space. The catheter assembly also includes a catheter tip that is connected to the second end portion. The catheter tip includes a housing that has a cavity defined therein. The catheter tip also includes a rotating element positioned within the cavity, wherein the rotating element is configured to rotate within the cavity to facilitate movement of the first end portion of the main body within the fluid filled space.

In another aspect, a shunt system for insertion into a body generally comprises a catheter assembly for inserting in a fluid filled space in the body and a control valve that is coupled in fluid communication with the catheter assembly. The control valve is configured to control the flow of fluid from the fluid filled space. The catheter assembly includes a main body that has a first end portion and a second end portion. The first end portion is positionable within the fluid filled space of the patient and the second end portion is adapted to extend outward from the fluid filled space when the first end portion is positioned within the fluid filled space. The catheter assembly also includes a catheter tip that is connected to the second end portion. The catheter tip includes a housing that has a cavity defined therein. The catheter tip also includes a rotating element positioned within the cavity, wherein the rotating element is configured to rotate within the cavity to facilitate movement of the first end portion of the main body within the fluid filled space.

In yet another aspect, a method of using a catheter assembly for inserting in a fluid filled space in a body generally comprises providing a main body having a first end portion and a second end portion. The first end portion is positioned within the fluid filled space. The second end portion is adjusted to extend outwardly from the fluid filled space when the first end portion is positioned within the fluid filled space. A catheter tip is connected to the second end portion. The catheter tip includes a housing having a cavity defined therein and a rotating element positioned within the cavity. The rotating element is rotated within the cavity of the housing to impart movement of the first end portion of the main body within the fluid filled space.

BRIEF DESCRIPTION OF THE DRAWINGS

FIG. 4 is a flow chart of an exemplary method of using the catheter assembly shown in FIG. 2.

DETAILED DESCRIPTION OF THE INVENTION

The exemplary systems, apparatus, and methods described herein overcome at least some known disadvantages associated with at least some known shunt systems that include the use of catheters, such as ventricular catheters. More specifically, the embodiments described herein include a catheter assembly for use in shunt systems, wherein the catheter assembly may be used for inserting in a fluid filled space of a body, while also inhibiting occlusion of the portions of the assembly that are located within the fluid filled space. The catheter assembly includes a main body that has a first end portion and a second end portion. The first end portion is positionable within the fluid filled space and the second end portion is adapted to extend outward from the fluid filled space when the first end portion is positioned within the fluid filled space. The catheter assembly also includes a catheter tip that is connected to the second end portion. The catheter tip includes a housing that has a cavity defined therein. The catheter tip also includes a rotating element positioned within the cavity, wherein the rotating element is configured rotate within the cavity to facilitate movement of the first end portion of the main body within the fluid filled space. By facilitating movement of at least a portion of the catheter assembly within the body, occlusion may be inhibited. More specifically, movement of the catheter assembly inhibits tissues located within the body from adhering to portions of the catheter assembly positioned within the fluid filled space. Accordingly, the catheter assembly enables the shunt system to adequately remove cerebrospinal fluid CSF from the brain.

Figure 1:
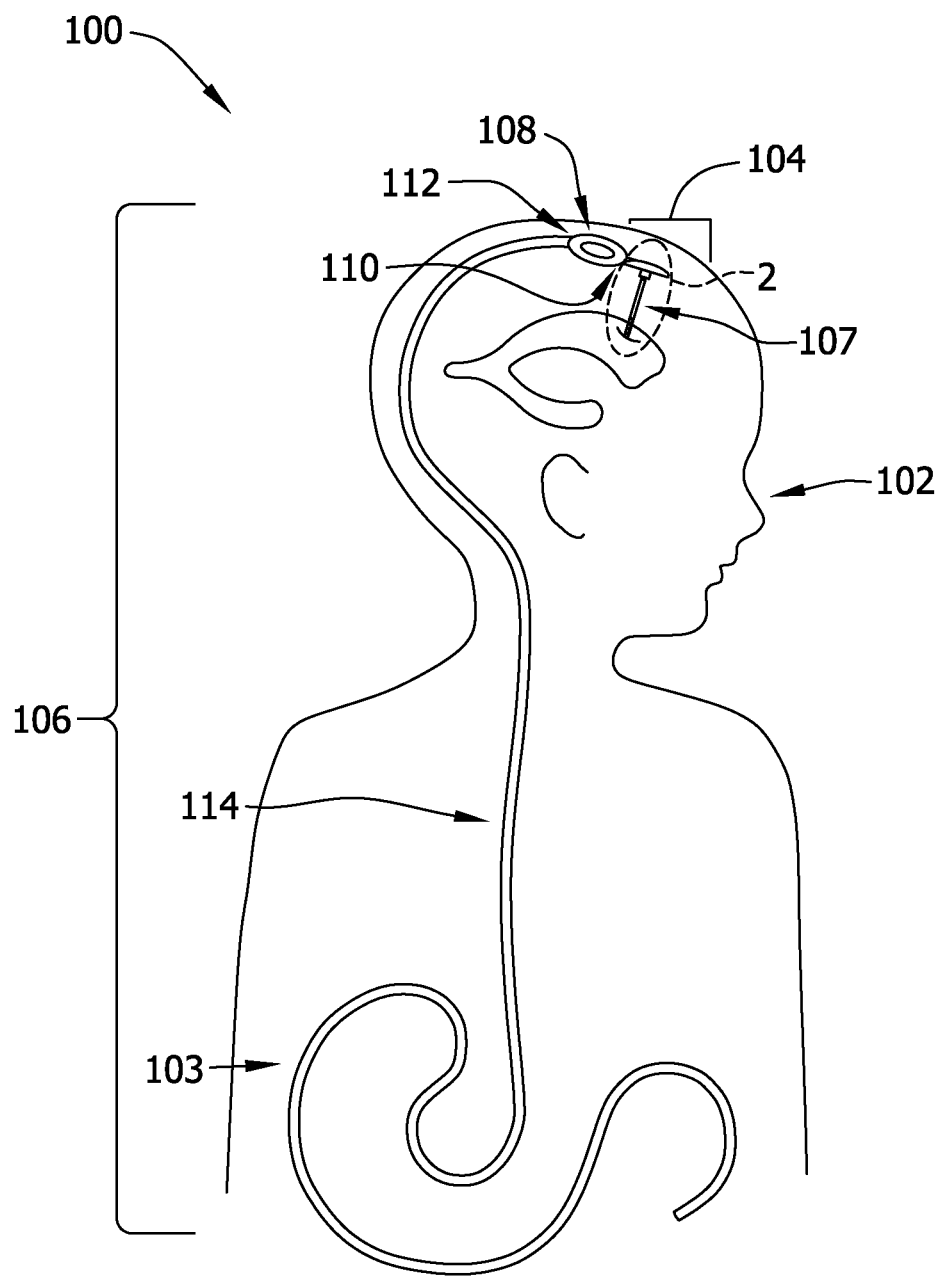
FIG. 1 is a schematic of an exemplary shunt system implanted in a patient.

FIG. 1 is a schematic of an exemplary shunt system 100 implanted in a patient 102. It should be noted that in the exemplary embodiment, shunt system 100 is a ventriculoperitoneal shunt system that facilitates fluid flow, such as cerebrospinal fluid (CSF), from at least one ventricle (not shown) of a brain of patient 102 to a peritoneal cavity 103 of patient 102. While the exemplary embodiment includes a ventriculoperitoneal shunt system, the embodiments of the systems, apparatus, and methods described herein are not limited to any one particular type of shunt system, and one of ordinary skill in the art will appreciate that the systems, apparatus, and methods described herein may be used in connection with other systems.

Shunt system 100 includes a proximal section 104 and a distal section 106, wherein a catheter assembly 107 is located within proximal section 104. In the exemplary embodiment, at least a portion (not shown in FIG. 1) of catheter assembly 107 is positioned within a fluid filled space within a body, such as a ventricle (not shown) of the brain in a body of patient 102. Fluid filled space may include a ventricle, a cyst, and/or an abscess within the body. In other embodiments, catheter assembly 107 may be positioned in other areas of patient 102 and at least a portion of catheter assembly 107 may be positioned within a ventricle located in other parts of patient 102, such as a heart ventricle. In addition, as explained in more detail below, catheter assembly 107 is configured to use motion of the head of patient 102 to impart movement to at least the portion of catheter assembly 107 within the ventricle. For example, the imparted movement may be rotational and/or linear.

Shunt system 100, in the exemplary embodiment, also includes a valve 108 positioned between proximal section 104 and distal section 106. In the exemplary embodiment, valve 108 includes a first end portion 110 and a second end portion 112, wherein first end portion 110 of valve 108 is coupled in flow communication with catheter assembly 107. Valve 108, in the exemplary embodiment, is configured to control the flow of a fluid, such as CSF, from the ventricle and within catheter assembly 107 to peritoneal cavity 103. For example, valve 108 may be a fixed pressure valve or, alternatively, valve 108 may be modulated in an open, partially open, closed, and/or partially closed position such that the flow of the fluid may vary within catheter assembly 107. Alternatively, valve 108 may be modulated in any other manner that enables shunt system 100 to function as described herein. In addition, valve 108 may be operated manually by a user and/or or valve 108 may be operated via a control system (not shown), such as a computing device, that may be communicatively coupled to valve 108.

In the exemplary embodiment, shunt system 100 also includes a distal catheter 114 that is positioned in distal section 106 and is coupled to second end portion 112 of valve 108. More specifically, in the exemplary embodiment, distal catheter 114 is positioned within the peritoneal cavity 103 of patient 102. In the exemplary embodiment, distal catheter 114 is configured to channel fluid, such as CSF, from catheter assembly 107 to peritoneal cavity 103. Alternatively, distal catheter 114 may be positioned in any other portion of patient 102, such as in the right atrium (not shown) of the heart (not shown), that enables shunt system 100 to function as described herein. Shunt system 100 may also be positioned outside patient 102. It should be noted that, as used herein, the term "couple" is not limited to a direct communicative, mechanical, and/or an electrical connection between components, but may also include an indirect communicative, mechanical, and/or electrical connection between multiple components.

During operation, shunt system 100 enables the removal of excess fluid from the brain. More specifically, by being positioned within the ventricle in the brain, catheter assembly 107 is able to channel fluid, such as CSF, from within the ventricle through valve 108 to distal catheter 114. The fluid is able to exit through distal catheter 114 to peritoneal cavity 103, wherein the fluid may be reabsorbed by the patient 102. As explained in more detail below, when the head of patient 102 moves, the motion enables catheter assembly 107 to impart movement to at least the portion of catheter assembly 107 within the ventricle. By facilitating movement of at least a portion of catheter assembly 107, occlusion may be inhibited. More specifically, movement of catheter assembly 107 inhibits tissues located within the brain from adhering to, or otherwise occluding, portions of catheter assembly 107 that are positioned within the ventricle. Accordingly, catheter assembly 107 enables shunt system 100 to adequately remove cerebrospinal fluid CSF from the brain.

Figure 2:
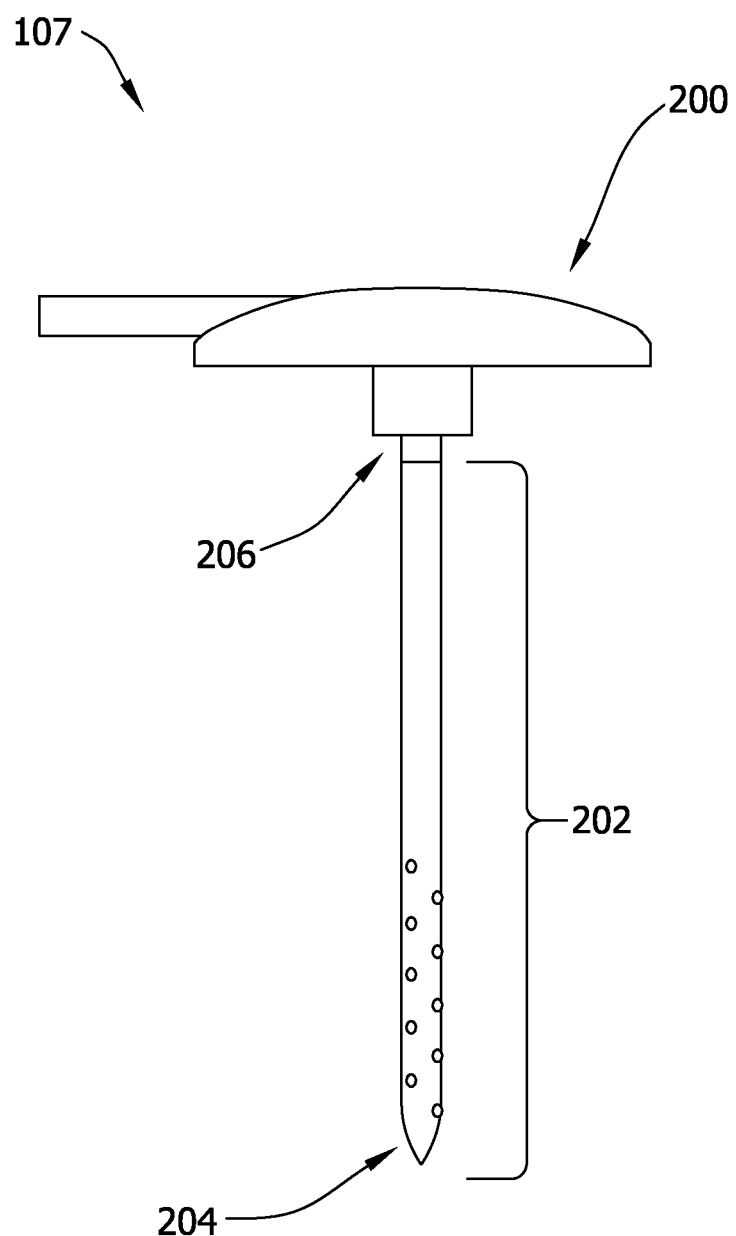
FIG. 2 is an enlarged view of one embodiment of a catheter assembly of the shunt system shown in FIG. 1 and taken from area 2.
Figure 3:
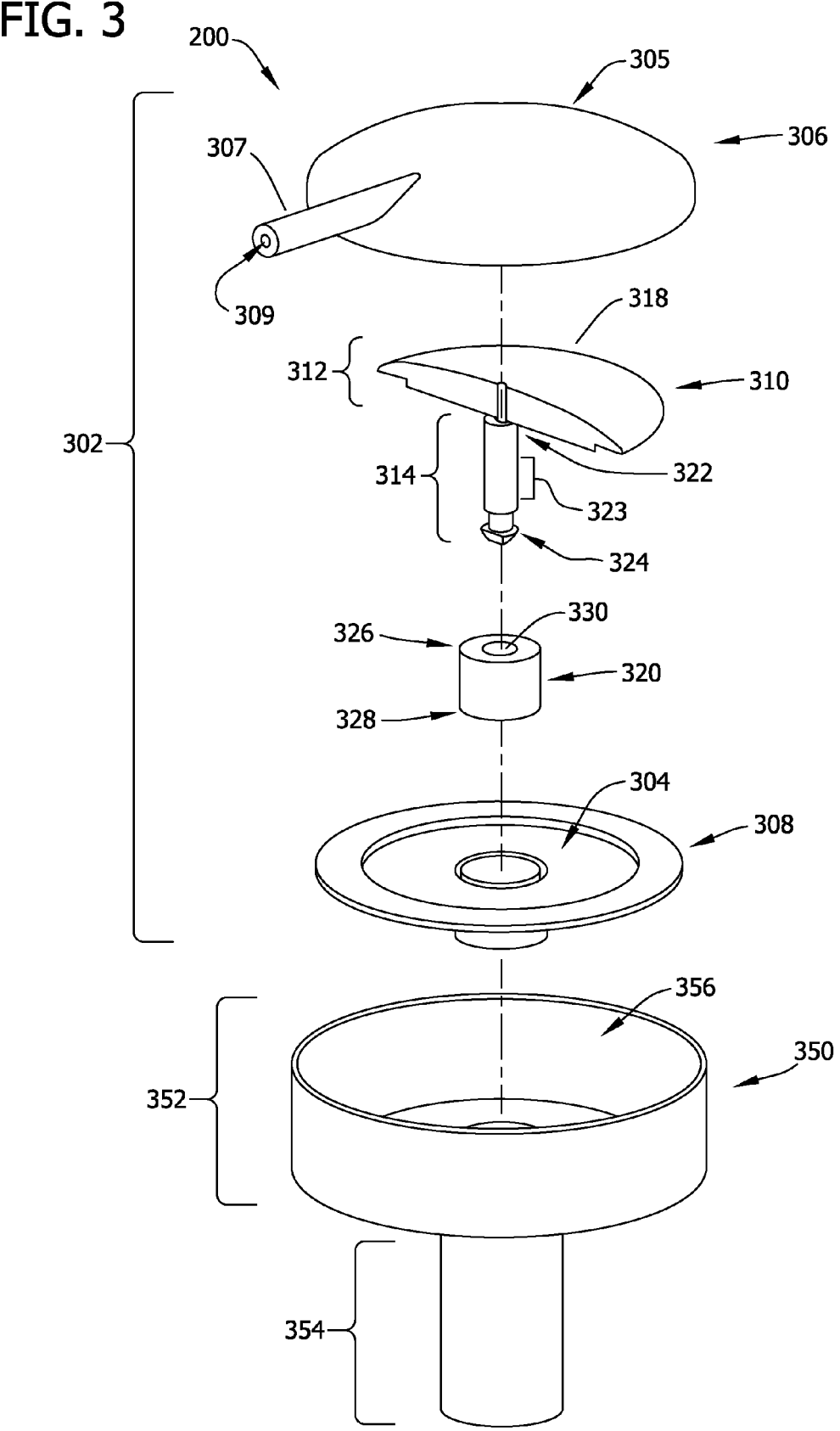
FIG. 3 is an exploded perspective view of a catheter tip of the catheter assembly shown in FIG. 2.

FIG. 2 is an enlarged view of catheter assembly 107 taken along area 2 (shown in FIG. 1) and removed from patient 102. FIG. 3 is an exploded perspective view of a catheter tip 200 of catheter assembly 107. Referring to FIG. 2, catheter assembly 107 includes a main body 202 having a first end portion 204 and a second end portion 206. In the exemplary embodiment, main body 202 is substantially cylindrical and hollow such that fluid may be channeled therethrough. However, main body 202 may be any suitable shape that enables catheter assembly 107 and shunt system 100 (shown in FIG. 1) to function as described herein.

Moreover, in the exemplary embodiment, main body 202 is substantially flexible, durable, and composed of any material that may be compatible with the fluid, such as CSF, being channeled therethrough, and suitable for implantation into patient 102. For example, main body 202 may be composed of polymers, such as, but not limited to silicone, polyurethane (PU), polyethylene (PE), polyvinylchloride (PVC), polytetrafluoroethylene (PTFE), and polyamides, such as nylon.

First end portion 204, in the exemplary embodiment, may be positioned within a ventricle of patient 102 (shown in FIG. 1) and second end portion 206 is adjusted or adapted to extend outward from the ventricle when first end portion 204 is positioned within the ventricle. Catheter tip 200, in the exemplary embodiment, is coupled to second end portion 206.

Referring to FIG. 3, catheter tip 200 includes a housing 302 having a cavity 304 defined therein. More specifically, housing 302 includes a cap member 306 and a base member 308 that is coupled to cap member 306 such that cavity 304 is defined between cap member 306 and base member 308. In the exemplary embodiment, cap member 306 includes a first portion 305 and a second portion 307 that extends outwardly from the first portion 305. Cap member first portion 305 is substantially semi-spherical and cap member second portion 307 is substantially cylindrical. Cap member 306 includes at least one opening 309 that extends axially through cap member second portion 307 such that fluid may be channeled therethrough.

Moreover, in the exemplary embodiment, cap member 306 is substantially flexible, durable, and composed of any material that may be compatible with the fluid, such as CSF, being channeled therein. For example, cap member 306 may be composed of polymers, such as, but not limited to silicone, polyurethane (PU), polyethylene (PE), polyvinylchloride (PVC), polytetrafluoroethylene (PTFE), and polyamides, such as nylon. In contrast, base member 308 is substantially rigid and may be composed of, for example, polyoxymethylene.

A rotating element 310 is positioned within cavity 304 and coupled to base member 308. More specifically, rotating element 310 is positioned within cavity 304 such that rotating element 310 is not in contact with any sides of cap member 306 and outlet path (not shown) may be defined between the rotating element 310 and the sides of cap member 306. In the exemplary embodiment, rotating element 310 is configured to facilitate movement of first end portion 204 (shown in FIG. 2) of main body 202 (shown in FIG. 2) within the ventricle. More specifically, rotating element 310 is configured to rotate in a single direction, such as a clockwise direction, to impart a rotational motion or a linear motion of first end portion 204 of main body 202. Alternatively, rotating element 310 may be configured to rotate in a first direction and a second direction, wherein the second direction is different from the first direction. For example, rotating element 310 may be configured to rotate in either a clockwise and/or counter-clockwise direction.

In the exemplary embodiment, rotating element 310 includes a first portion 312 and a second portion 314 that is coupled to first portion 312 such that second portion 314 is perpendicular to first portion 312. More specifically, rotating element first portion 312 includes an upstream surface 316 and an opposing downstream surface 318, and rotating element second portion 314 is coupled to upstream surface 316 while downstream surface 318 faces cap member 306. First portion 312 and second portion 314 may be removably coupled with respect to each other, or first portion 312 and second portion 314 may be integrally formed together as a single piece. In the exemplary embodiment, both upstream surface 316 and downstream surface 318 have a substantially semi-circular shape. Alternatively, upstream surface 316 and downstream surface 318 may have other suited shapes that enable catheter assembly 107 (shown in FIGS. 1 and 2) and/or shunt system 100 (shown in FIG. 1) to function as described herein. In the exemplary embodiment, at least a portion of rotating element 310, such as first portion 312, is composed of a substantially dense chemical element, such as but not limited to tantalum, gold, titanium, and/or steel.

Rotating element second portion 314 is coupled to base member 308 via a bearing portion 320. In the exemplary embodiment, rotating element second portion 314 is a connecting device that is configured to enable catheter tip 200 to be coupled to second end portion 206 (shown in FIG. 2) of main body 202. Rotating element second portion 314, in the exemplary embodiment, includes a first end 322, a middle portion 323, and a second end 324. First end 322 is coupled to upstream surface 316 of rotating element 310. Rotating element second portion 314 is substantially cylindrical and hollow from first end 322 to middle portion 323. Rotating element second end 324 is configured to be coupled to second end portion 206 of main body 202. For example, second end 324 may have a substantially nipple shape to enable second end 324 to be securely positioned within second end portion 206 of main body 202. Alternatively, rotating element second portion 314 and any portions thereof may have any other suitable shape that enables catheter tip 200 to be coupled to main body 202. Moreover, rotating element second portion 314 may be composed of the same chemical element as rotating element first portion 312. Alternatively, rotating element second portion 314 may be composed of a different chemical element than rotating element first portion 312. For example, second portion 314 may be composed of steel, while the first portion 312 is composed of tantalum. It is preferable that both first portion 312 and second portion 314 of rotating element 310 be composed of a substantially dense chemical element or compound.

In the exemplary embodiment, bearing portion 320 is an annular tube having a first end 326 and a second end 328. Moreover, in the exemplary embodiment, bearing portion 320 is substantially cylindrical and includes an opening 330 that extends from first end 326 to second end 328 such that at least a portion of rotating element second portion 314 may be positioned therein. Bearing portion 320, however, may be any suitable shape that enables catheter assembly 107 to function as described herein. Bearing portion 320, in the exemplary embodiment, is coupled to second portion 314 of rotating element 310 and to base member 308 such that a seal within cavity 304 is formed and fluid does not leak from within cavity 304. In the exemplary embodiment, bearing portion 320 may be composed of an alloy, such as but not limited to steel.

Catheter assembly 107 may also include a sleeve portion 350 that substantially circumscribes at least a portion of catheter tip 200 and at least a portion of main body 202. More specifically, in the exemplary embodiment, sleeve portion 350 includes a first portion 352 and a second portion 354. First portion 352 includes a cavity 356 defined therein such that rotating element 310, bearing portion 320, and base member 308 may be positioned within cavity 356. Second portion 354 is substantially cylindrical and hollow such that second portion 354 may substantially circumscribe main body second end portion 206 (shown in FIG. 2). In the exemplary embodiment, sleeve portion 350 may be substantially flexible, durable, and composed of any material that may be compatible with the fluid, such as CSF, being channeled within catheter assembly 107, and suitable for implantation into patient 102. For example, sleeve portion 350 may be composed of polymers, such as, but not limited to silicone, polyurethane (PU), polyethylene (PE), polyvinylchloride (PVC), polytetrafluoroethylene (PTFE), and polyamides, such as nylon.

During operation, excess fluid within the brain, such as CSF, is channeled from a ventricle through main body 202 of catheter assembly 107. More specifically, fluid is channeled from first end portion 204 of main body 202 to second end portion 206. Fluid is then channeled to catheter tip 200. For example, fluid may be channeled through base member 308 to cap member 306. Fluid may then be channeled through opening 309 within second portion 307 of cap member 306. Fluid is channeled through valve 108 (shown in FIG. 1) to distal catheter 114 (shown in FIG. 1). When fluid is channeled within distal catheter 114, fluid is able to exit through distal catheter 114 to peritoneal cavity 103 (shown in FIG. 1), wherein the fluid is reabsorbed.

When the head of the patient 102 moves, the catheter assembly 107 is enabled to move. More specifically, the kinetic energy from the natural movement of the head applies a force, such as a centripetal force, to rotating element 310. In the exemplary embodiment, such a force enables first portion 312 of rotating element 310 to move in a single direction, such as in a clockwise direction. It is understood, however, that the force may enable first portion 312 of rotating element 310 to move in either a clockwise and/or counter-clockwise direction.

As first portion 312 of rotating element 310 rotates within cavity 304, second portion 314 of rotating element 310 is enabled to rotate in the same direction as first portion 312. Since second portion 314 of rotating element 310 is coupled to second end portion 206 of main body 202, when rotating element 310 rotates, at least a portion of main body 202 is able to move. More specifically, in the exemplary embodiment, as rotating element 310 rotates, first end portion 204 of main body 202 is able to rotate within the ventricle. Alternatively, first end portion 204 of main body 202 may be able to move in a linear motion within the ventricle. In another embodiment, a magnet (not shown) may be inserted within rotating element 310. In such an embodiment, an external magnet (not shown) may be used to enable rotating element 310 to rotate.

By facilitating the movement of first end portion 204, occlusion may be inhibited. More specifically, the movement of first end portion 204 prevents tissues located within the brain from adhering to, or otherwise occluding, portions of first end portion 204. Moreover, when catheter assembly 107 is moving, sleeve portion 350 substantially reduces the friction between the brain and portions of catheter assembly 107 that are not positioned within the ventricle. More specifically, sleeve portion 350 substantially reduces the friction between the brain and portions of catheter tip 200 and main body 202 that are circumscribed by sleeve portion 350 such that catheter assembly 107 is not inhibited from rotating within the brain.

FIG. 4 illustrates a flow chart of an exemplary method 400 of using a catheter assembly, such as catheter assembly 107 (shown in FIGS. 1 and 2). A main body 202 (shown in FIG. 2) having a first end portion 204 (shown in FIG. 2) and a second end portion 206 (shown in FIG. 2) is provided 402. Main body first end portion 204 is positioned 404 within a ventricle (not shown), such as a ventricle in a brain, of a patient 102 (shown in FIG. 1). When main body first end portion 204 is positioned 404 within the ventricle, main body second end portion 206 is adjusted 406 to extend outwardly from the ventricle. A catheter tip 200 (shown in FIGS. 2 and 3) is connected 408 to main body second end portion 206, wherein catheter tip 200 includes a housing 302 (shown in FIG. 3) having a cavity 304 (shown in FIG. 3) defined therein and a rotating element 310 (shown in FIG. 3) is positioned within cavity 304. Rotating element 310 is rotated 410 within cavity 304 to impart a movement of main body first end portion 204 within the ventricle.

When rotating element 310 is rotated 410 within cavity 304, rotating element 310 is rotated 412 in a single direction. Alternatively, when rotating element 310 is rotated 410 within cavity 304, rotating element 310 is rotated 414 in a first direction or a second direction, wherein the first direction is different from the second direction. Moreover, when rotating element 310 is rotated 410 within cavity 304, rotating element 310 imparts 416 a rotational motion and or a linear motion to main body first end portion 204.

The above-described shunt system includes a catheter assembly that may be inserted in a fluid filled space in a body, while inhibiting occlusion of the portions of the assembly that are located within the fluid filled space. The catheter assembly includes a main body that has a first end portion and a second end portion. The first end portion is positionable within the fluid filled space of the patient and the second end portion is adapted to extend outward from the fluid filled space when the first end portion is positioned within the fluid filled space. The catheter assembly also includes a catheter tip that is connected to the second end portion. The catheter tip includes a housing that has a cavity defined therein. The catheter tip also includes a rotating element positioned within the cavity, wherein the rotating element is configured to rotate within the cavity to facilitate movement of the first end portion of the main body within the fluid filled space. By facilitating movement of at least a portion of the catheter assembly within the body, occlusion may be prevented. More specifically, the movement of the catheter assembly prevents tissues located within the body from adhering to, or otherwise occluding, portions of the catheter assembly that are positioned within the fluid filled space.

Exemplary embodiments of a catheter assembly and method of using same are described above in detail. The catheter assembly and method of using same are not limited to the specific embodiments described herein, but rather, components of the catheter assembly and/or steps of the method may be utilized independently and separately from other components and/or steps described herein. For example, the catheter assembly may also be used in combination with other systems and methods, and is not limited to practice with only a shunt system as described herein. Rather, the exemplary embodiment can be implemented and utilized in connection with many other systems.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A catheter assembly for inserting in a fluid filled space in a body, the catheter assembly comprising:
    a main body having a first end portion and a second end portion, the first end portion being positionable within the fluid filled space and the second end portion being adapted to extend outward from the fluid filled space when the first end portion is positioned within the fluid filled space; and
    a catheter tip connected to the second end portion, the catheter tip comprising:
    a housing having a cavity defined therein; and a rotating element positioned within the cavity, wherein the rotating element being connected to the first end portion of the main body such that rotation of the rotating element results in at least one of rotational and linear movement, relative to the housing which has no movement imparted to it, of the first end portion of the main body within the fluid filled space.

2. A catheter assembly in accordance with claim 1, wherein the rotating element is configured to rotate in a single direction.

3. A catheter assembly in accordance with claim 1, wherein the housing comprises:
    a cap member; and
    a base member coupled to the cap member such that the cavity is defined therebetween.

4. A catheter assembly in accordance with claim 3, wherein the catheter tip further comprises a bearing portion coupled to the base member and to the rotating element, the bearing portion being configured to seal the cavity.

5. A catheter assembly in accordance with claim 1, wherein the rotating element comprises a connecting device for connecting the catheter tip to the second end portion of the main body.

6. A catheter assembly in accordance with claim 1, wherein the rotating element is made of at least one of tungsten, gold, titanium, tantalum, and steel.

7. A catheter assembly in accordance with claim 1, further comprising a sleeve portion to substantially circumscribe at least a portion of the catheter tip and at least a portion of the main body.

8. A shunt system for insertion into a body, the shunt system comprising:
a catheter assembly for inserting in a fluid filled space in the body, the catheter assembly comprising:
a main body having a first end portion and a second end portion, the first end portion being positionable within the fluid filled space and the second end portion being adapted to extend outward from the fluid filled space when the first end portion is positioned within the fluid filled space; and a catheter tip connected to the second end portion, the catheter tip comprising:
a housing having a cavity defined therein; and a rotating element positioned within the cavity, the rotating element being connected to the first end portion of the main body such that rotation of the rotating element results in at least one of rotational and movement of the first end portion of the main body within the fluid filled space relative to the housing which has no movement imparted to it, and
a control valve in fluid communication with the catheter assembly and configured to control the flow of fluid from the fluid filled space.

9. A shunt system in accordance with claim 8, wherein the rotating element is configured to rotate in a single direction.

10. A shunt system in accordance with claim 8, wherein the housing comprises:
a cap member; and
a base member coupled to the cap member such that the cavity is defined therebetween.

11. A shunt system in accordance with claim 10, wherein the catheter tip further comprises a bearing portion coupled to the base member and to the rotating element, the bearing portion being configured to seal the cavity.

12. A shunt system in accordance with claim 8, wherein the rotating element comprises a connecting device for connecting the catheter tip to the second end portion of the main body.

13. A shunt system in accordance with claim 8, wherein the rotating element is made of at least one of tungsten, gold, titanium, tantalum, and steel.

14. A catheter assembly in accordance with claim 1, wherein the rotating element has an upstream surface and a downstream surface, both of the upstream and downstream surfaces being semi-circular in shape.

15. A shunt system in accordance with claim 8, wherein the rotating element has an upstream surface and a downstream surface, both of the upstream and downstream surfaces being semi-circular in shape.

* * * * *